US012324925B2

(12) United States Patent
Orinski

(10) Patent No.: US 12,324,925 B2
(45) Date of Patent: *Jun. 10, 2025

(54) IMPLANTABLE OPTICAL STIMULATION LEAD AND METHODS OF MAKING AND USING

(71) Applicant: Boston Scientific Neuromodulation Corporation, Valencia, CA (US)

(72) Inventor: William George Orinski, Reno, NV (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 100 days.

This patent is subject to a terminal disclaimer.

(21) Appl. No.: 17/964,740

(22) Filed: Oct. 12, 2022

(65) Prior Publication Data

US 2023/0034868 A1     Feb. 2, 2023

Related U.S. Application Data

(63) Continuation of application No. 16/412,157, filed on May 14, 2019, now Pat. No. 11,511,127, which is a (Continued)

(51) Int. Cl.
*A61N 5/06* (2006.01)
*A61N 1/05* (2006.01)
(Continued)

(52) U.S. Cl.
CPC ............. *A61N 5/0601* (2013.01); *A61N 1/05* (2013.01); *A61N 1/3754* (2013.01);
(Continued)

(58) Field of Classification Search
CPC .................... A61N 5/06; A61N 5/0601; A61N 2005/0612; A61N 5/0622;
(Continued)

(56) References Cited

U.S. PATENT DOCUMENTS 4,920,979 A    5/1990  Bullara
5,076,270 A    12/1991  Stutz, Jr.
(Continued)

FOREIGN PATENT DOCUMENTS

EP      2143373 A1    1/2010
EP     30204501 A1    5/2016
(Continued)

OTHER PUBLICATIONS

Baxter, G.D. et al., Effects of Low Intensity Infrared Laser Irradiation Upon Conduction in the Human Median Nerve In Vivo, Experimental Physiology (1994) 79, 227-234.
(Continued)

*Primary Examiner* — Ahmed M Farah
(74) *Attorney, Agent, or Firm* — Branch Partners PLLC; Bruce E. Black

(57) ABSTRACT

An optical stimulation lead includes a lead body including a distal end, a distal portion, and a proximal portion; and an optical assembly attached to the distal end of the lead body. The optical assembly includes a light emitter; a feedthrough assembly including at least one ceramic block, at least one feedthrough pin extending through the at least one ceramic block and electrically coupled to the light emitter, and a metal housing attached to the at least one ceramic block; a metal tube attached to the feedthrough assembly and disposed around the light emitter; and an emitter cover disposed over the light emitter and coupled to the metal tube.

20 Claims, 7 Drawing Sheets

Related U.S. Application Data continuation of application No. 15/421,001, filed on Jan. 31, 2017, now Pat. No. 10,335,607.

(60) Provisional application No. 62/424,130, filed on Nov. 18, 2016, provisional application No. 62/292,083, filed on Feb. 5, 2016.

(51) Int. Cl.
  *A61N 1/375* (2006.01)
  *A61N 1/36* (2006.01)
  *A61N 5/067* (2006.01)

(52) U.S. Cl.
  CPC ........ *A61N 5/0622* (2013.01); *A61N 1/36025* (2013.01); *A61N 2005/0612* (2013.01); *A61N 2005/0651* (2013.01); *A61N 2005/0653* (2013.01); *A61N 5/067* (2021.08)

(58) Field of Classification Search
  CPC ...... A61N 2005/063; A61N 2005/0632; A61N 2005/0643; A61N 2005/065; A61N 2005/0651; A61N 2005/067; A61N 1/05; A61N 1/36025; A61N 1/3605; A61N 1/372; A61N 1/37514; A61N 1/3752; A61N 1/3754; A61N 5/067; A61N 2005/0653
  USPC .................................................. 607/88–90, 92
  See application file for complete search history.

(56) References Cited

U.S. PATENT DOCUMENTS

| | | | |
|---|---|---|---|
| 5,437,193 | A | 8/1995 | Schleitweiler et al. |
| 5,445,608 | A * | 8/1995 | Chen .................. A61N 5/062 604/20 |
| 5,556,421 | A | 9/1996 | Prutchi et al. |
| 5,824,027 | A | 10/1998 | Hoffer et al. |
| 6,175,710 | B1 | 1/2001 | Kamaji et al. |
| 6,181,969 | B1 | 1/2001 | Gord |
| 6,224,450 | B1 | 5/2001 | Norton |
| 6,271,094 | B1 | 8/2001 | Boyd et al. |
| 6,295,944 | B1 | 10/2001 | Lovett |
| 6,364,278 | B1 | 4/2002 | Lin et al. |
| 6,366,719 | B1 | 4/2002 | Heath et al. |
| 6,391,985 | B1 | 5/2002 | Goode et al. |
| 6,442,435 | B2 | 8/2002 | King et al. |
| 6,516,227 | B1 | 2/2003 | Meadows et al. |
| 6,609,029 | B1 | 8/2003 | Mann et al. |
| 6,609,032 | B1 | 8/2003 | Woods et al. |
| 6,741,892 | B1 | 5/2004 | Meadows et al. |
| 6,895,280 | B2 | 5/2005 | Meadows et al. |
| 6,988,001 | B2 * | 1/2006 | Greatbatch ............ A61N 1/056 607/9 |
| 6,993,384 | B2 | 1/2006 | Bradley et al. |
| 7,190,993 | B2 | 3/2007 | Sharma et al. |
| 7,203,548 | B2 | 4/2007 | Whitehurst et al. |
| 7,244,150 | B1 | 7/2007 | Brase et al. |
| 7,252,677 | B2 | 8/2007 | Burwell et al. |
| 7,288,108 | B2 | 10/2007 | DiMauro et al. |
| 7,395,118 | B2 | 7/2008 | Erickson |
| 7,437,193 | B2 | 10/2008 | Parramon et al. |
| 7,450,997 | B1 | 11/2008 | Pianca et al. |
| 7,596,414 | B2 | 9/2009 | Whitehurst et al. |
| 7,610,103 | B2 | 10/2009 | Whitehurst et al. |
| 7,672,734 | B2 | 3/2010 | Anderson et al. |
| 7,684,869 | B2 | 3/2010 | Bradley et al. |
| 7,736,382 | B2 | 6/2010 | Webb et al. |
| 7,761,165 | B1 | 7/2010 | He et al. |
| 7,783,359 | B2 | 8/2010 | Meadows |
| 7,792,590 | B1 | 9/2010 | Pianca et al. |
| 7,803,021 | B1 | 9/2010 | Brase |
| 7,809,435 | B1 | 10/2010 | Ettare et al. |
| 7,809,446 | B2 | 10/2010 | Meadows |
| 7,946,980 | B2 | 5/2011 | Reddy et al. |
| 7,949,395 | B2 | 5/2011 | Kuzma |
| 7,949,409 | B2 | 5/2011 | Bly et al. |
| 7,974,706 | B2 | 7/2011 | Moffitt et al. |
| 8,086,322 | B2 | 12/2011 | Schouenborg |
| 8,175,710 | B2 | 5/2012 | He |
| 8,224,450 | B2 | 7/2012 | Brase |
| 8,271,094 | B1 | 9/2012 | Moffitt et al. |
| 8,295,944 | B2 | 10/2012 | Howard et al. |
| 8,311,647 | B2 | 11/2012 | Bly |
| 8,326,433 | B2 | 12/2012 | Blum et al. |
| 8,340,785 | B2 | 12/2012 | Bonde et al. |
| 8,364,278 | B2 | 1/2013 | Pianca et al. |
| 8,386,054 | B2 | 2/2013 | North |
| 8,391,985 | B2 | 3/2013 | McDonald |
| 8,463,343 | B2 | 6/2013 | Kuhn et al. |
| 8,473,061 | B2 | 6/2013 | Moffitt et al. |
| 8,483,237 | B2 | 7/2013 | Zimmermann et al. |
| 8,525,027 | B2 | 9/2013 | Lindner et al. |
| 8,571,665 | B2 | 10/2013 | Moffitt et al. |
| 8,600,509 | B2 | 12/2013 | McDonald et al. |
| 8,675,945 | B2 | 3/2014 | Barnhorst et al. |
| 8,682,439 | B2 | 3/2014 | DeRohan et al. |
| 8,688,235 | B1 | 4/2014 | Pianca et al. |
| 8,792,993 | B2 | 7/2014 | Pianca et al. |
| 8,831,731 | B2 | 9/2014 | Blum et al. |
| 8,831,742 | B2 | 9/2014 | Pianca et al. |
| 8,831,746 | B2 | 9/2014 | Swanson |
| 8,849,632 | B2 | 9/2014 | Sparks et al. |
| 8,855,768 | B1 | 10/2014 | Johnson et al. |
| 8,868,211 | B2 | 10/2014 | Durand et al. |
| 8,897,876 | B2 | 11/2014 | Sundaramurthy et al. |
| 8,929,973 | B1 | 1/2015 | Webb et al. |
| 8,936,630 | B2 | 1/2015 | Denison et al. |
| 8,958,615 | B2 | 2/2015 | Blum et al. |
| 9,238,132 | B2 | 1/2016 | Barker |
| 9,409,032 | B2 | 8/2016 | Brase et al. |
| 9,415,154 | B2 | 8/2016 | Leven |
| 9,421,362 | B2 | 8/2016 | Seeley |
| 9,440,066 | B2 | 9/2016 | Black |
| 9,550,063 | B2 | 1/2017 | Wolf, II |
| 9,604,068 | B2 | 3/2017 | Malinowski |
| 9,643,010 | B2 | 5/2017 | Ranu |
| 9,656,093 | B2 | 5/2017 | Villarta et al. |
| 9,681,809 | B2 | 6/2017 | Sharma et al. |
| 9,770,598 | B2 | 9/2017 | Malinowski et al. |
| 9,931,511 | B2 | 4/2018 | Kaula et al. |
| 10,213,596 | B2 * | 2/2019 | Orinski .............. A61N 1/37211 |
| 10,307,602 | B2 | 6/2019 | Leven |
| 10,335,607 | B2 * | 7/2019 | Orinski ................ A61N 5/0601 |
| 10,471,273 | B2 | 11/2019 | Segev et al. |
| 10,644,194 | B2 | 5/2020 | Kim et al. |
| 10,814,140 | B2 | 10/2020 | Zhang et al. |
| 11,395,923 | B2 | 7/2022 | Lu et al. |
| 11,511,127 | B2 * | 11/2022 | Orinski ................ A61N 5/0622 |
| 2002/0156513 | A1 | 10/2002 | Borkan |
| 2002/0161417 | A1 | 10/2002 | Scribner |
| 2004/0098063 | A1 | 5/2004 | Goetz |
| 2004/0147964 | A1 | 7/2004 | Nolan et al. |
| 2005/0096720 | A1 | 5/2005 | Sharma et al. |
| 2005/0216072 | A1 | 9/2005 | Mahadevan-Jansen et al. |
| 2006/0129210 | A1 | 6/2006 | Cantin et al. |
| 2006/0155348 | A1 | 7/2006 | deCharms |
| 2006/0161227 | A1 | 7/2006 | Walsh et al. |
| 2007/0053996 | A1 | 3/2007 | Boyden et al. |
| 2007/0100398 | A1 | 5/2007 | Sloan |
| 2007/0150036 | A1 | 6/2007 | Anderson |
| 2007/0161919 | A1 | 7/2007 | DiLorenzo |
| 2007/0208395 | A1 | 9/2007 | Leclerc et al. |
| 2007/0244524 | A1 | 10/2007 | Qu et al. |
| 2007/0244526 | A1 | 10/2007 | Zaghetto et al. |
| 2008/0046053 | A1 | 2/2008 | Wagner et al. |
| 2008/0077198 | A1 | 3/2008 | Webb et al. |
| 2008/0146890 | A1 | 6/2008 | LeBoeuf et al. |
| 2008/0167701 | A1 | 7/2008 | John et al. |
| 2008/0197300 | A1 | 8/2008 | Kayser et al. |
| 2008/0243218 | A1 | 10/2008 | Bottomley et al. |
| 2009/0054954 | A1 | 2/2009 | Foley et al. |
| 2009/0054955 | A1 | 2/2009 | Kopell et al. |

(56) References Cited

U.S. PATENT DOCUMENTS

| | | |
|---|---|---|
| 2009/0069871 A1 | 3/2009 | Mahadevan-Jansen et al. |
| 2009/0118800 A1 | 5/2009 | Deisseroth et al. |
| 2009/0187222 A1 | 7/2009 | Barker |
| 2009/0196471 A1 | 8/2009 | Goetz et al. |
| 2009/0276021 A1 | 11/2009 | Meadows et al. |
| 2009/0287272 A1 | 11/2009 | Kokones et al. |
| 2009/0287273 A1 | 11/2009 | Carlton et al. |
| 2009/0299447 A1 | 12/2009 | Jensen et al. |
| 2010/0076508 A1 | 3/2010 | McDonald et al. |
| 2010/0076535 A1 | 3/2010 | Pianca et al. |
| 2010/0094364 A1 | 4/2010 | McDonald |
| 2010/0105997 A1 | 4/2010 | Ecker et al. |
| 2010/0114190 A1 | 5/2010 | Bendett et al. |
| 2010/0174329 A1 | 7/2010 | Dadd et al. |
| 2010/0174344 A1 | 7/2010 | Dadd et al. |
| 2010/0256693 A1 | 10/2010 | McDonald et al. |
| 2010/0268298 A1 | 10/2010 | Moffitt et al. |
| 2010/0292758 A1 | 11/2010 | Lee et al. |
| 2010/0292759 A1 | 11/2010 | Lee et al. |
| 2010/0324630 A1 | 12/2010 | Lee et al. |
| 2010/0326701 A1 | 12/2010 | McDonald |
| 2011/0004267 A1 | 1/2011 | Meadows |
| 2011/0005069 A1 | 1/2011 | Pianca |
| 2011/0009932 A1 | 1/2011 | McDonald et al. |
| 2011/0022100 A1 | 1/2011 | Brase et al. |
| 2011/0029055 A1 | 2/2011 | Tidemand |
| 2011/0046432 A1 | 2/2011 | Simon et al. |
| 2011/0046700 A1 | 2/2011 | McDonald et al. |
| 2011/0078900 A1 | 4/2011 | Pianca et al. |
| 2011/0106208 A1 | 5/2011 | Faltys et al. |
| 2011/0112591 A1 | 5/2011 | Seymour et al. |
| 2011/0125077 A1 | 5/2011 | Denison et al. |
| 2011/0125078 A1 | 5/2011 | Denison et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0172653 A1 | 7/2011 | Schneider et al. |
| 2011/0172725 A1 | 7/2011 | Wells et al. |
| 2011/0238129 A1 | 9/2011 | Moffitt et al. |
| 2011/0295331 A1 | 12/2011 | Wells et al. |
| 2011/0313500 A1 | 12/2011 | Barker et al. |
| 2012/0014580 A1 | 1/2012 | Blum et al. |
| 2012/0016378 A1 | 1/2012 | Pianca et al. |
| 2012/0046710 A1 | 2/2012 | Digiore et al. |
| 2012/0046715 A1 | 2/2012 | Moffitt et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0232354 A1 | 9/2012 | Ecker et al. |
| 2012/0253261 A1 | 10/2012 | Poletto et al. |
| 2012/0265262 A1 | 10/2012 | Osorio |
| 2012/0265268 A1 | 10/2012 | Blum et al. |
| 2012/0287420 A1 | 11/2012 | McLaughlin et al. |
| 2012/0314924 A1 | 12/2012 | Carlton et al. |
| 2012/0316615 A1 | 12/2012 | Digiore et al. |
| 2013/0019325 A1 | 1/2013 | Deisseroth et al. |
| 2013/0053905 A1 | 2/2013 | Wagner |
| 2013/0079848 A1 | 3/2013 | Campbell et al. |
| 2013/0102861 A1 | 4/2013 | Oki et al. |
| 2013/0105071 A1 | 5/2013 | Digiore et al. |
| 2013/0116744 A1 | 5/2013 | Blum et al. |
| 2013/0184794 A1* | 7/2013 | Feldman ............... A61N 1/05 607/116 |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0281819 A1 | 10/2013 | Schmid |
| 2013/0304152 A1 | 11/2013 | Bradley et al. |
| 2013/0317572 A1 | 11/2013 | Zhu et al. |
| 2013/0317573 A1 | 11/2013 | Zhu et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0067015 A1 | 3/2014 | Kothandaraman et al. |
| 2014/0067023 A1 | 3/2014 | Register et al. |
| 2014/0074182 A1 | 3/2014 | Wolf, II |
| 2014/0114150 A1 | 4/2014 | Pogue et al. |
| 2014/0122379 A1 | 5/2014 | Moffitt et al. |
| 2014/0142664 A1 | 5/2014 | Roukes et al. |
| 2014/0163639 A1 | 6/2014 | Zhu |
| 2014/0200639 A1 | 7/2014 | De La Rama |
| 2014/0296953 A1 | 10/2014 | Pianca et al. |
| 2014/0330341 A1 | 11/2014 | Wolf, II |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0005680 A1 | 1/2015 | Lipani |
| 2015/0005860 A1 | 1/2015 | Howard et al. |
| 2015/0018915 A1 | 1/2015 | Leven |
| 2015/0021817 A1 | 1/2015 | Romero et al. |
| 2015/0045862 A1* | 2/2015 | Goldman ............. A61N 1/3754 607/116 |
| 2015/0045864 A1 | 2/2015 | Howard |
| 2015/0051676 A1* | 2/2015 | Van Funderburk ..... C03C 27/08 607/116 |
| 2015/0051681 A1 | 2/2015 | Hershey |
| 2015/0066111 A1 | 3/2015 | Blum et al. |
| 2015/0066120 A1 | 3/2015 | Govea |
| 2015/0080757 A1 | 3/2015 | Torisawa et al. |
| 2015/0151113 A1 | 6/2015 | Govea et al. |
| 2015/0202456 A1 | 7/2015 | Andersen et al. |
| 2015/0290461 A1 | 10/2015 | Min et al. |
| 2015/0306414 A1 | 10/2015 | Nielsen et al. |
| 2015/0360031 A1 | 12/2015 | Bornzin et al. |
| 2015/0375006 A1 | 12/2015 | Denison et al. |
| 2016/0030749 A1 | 2/2016 | Carcieri et al. |
| 2016/0045740 A1 | 2/2016 | Rezai et al. |
| 2016/0067519 A1 | 3/2016 | Tranberg et al. |
| 2016/0082251 A1 | 3/2016 | Moffitt et al. |
| 2016/0082253 A1 | 3/2016 | Moffitt et al. |
| 2016/0151639 A1 | 6/2016 | Scharf et al. |
| 2016/0228692 A1 | 8/2016 | Steinke et al. |
| 2016/0250474 A1 | 9/2016 | Stack et al. |
| 2016/0250497 A1 | 9/2016 | Jay |
| 2016/0256689 A1 | 9/2016 | Vallejo et al. |
| 2016/0271392 A1 | 9/2016 | Vallejo et al. |
| 2016/0271413 A1 | 9/2016 | Vallejo et al. |
| 2016/0287885 A1 | 10/2016 | Saini |
| 2016/0296745 A1 | 10/2016 | Govea et al. |
| 2016/0331994 A1 | 11/2016 | Smith et al. |
| 2016/0346557 A1 | 12/2016 | Bokil |
| 2016/0361543 A1 | 12/2016 | Kaula et al. |
| 2016/0375258 A1 | 12/2016 | Steinke |
| 2017/0000419 A1 | 1/2017 | Schouenborg |
| 2017/0061627 A1 | 3/2017 | Bokil |
| 2017/0095670 A1 | 4/2017 | Ghaffari et al. |
| 2017/0100580 A1 | 4/2017 | Olson |
| 2017/0136254 A1 | 5/2017 | Simon et al. |
| 2017/0143985 A1 | 5/2017 | Degenaar et al. |
| 2017/0172446 A1 | 6/2017 | Kuzum et al. |
| 2017/0182191 A1 | 6/2017 | Towne et al. |
| 2017/0259078 A1 | 9/2017 | Howard |
| 2017/0281928 A1* | 10/2017 | Orinski ............... A61N 1/0539 |
| 2017/0281966 A1 | 10/2017 | Basiony |
| 2017/0304633 A1 | 10/2017 | Zhang |
| 2017/0348522 A1 | 12/2017 | Stoffregen et al. |
| 2017/0361108 A1 | 12/2017 | Leven |
| 2017/0361122 A1 | 12/2017 | Chabrol et al. |
| 2018/0028820 A1 | 2/2018 | Nageri |
| 2018/0064930 A1 | 3/2018 | Zhang et al. |
| 2018/0078776 A1 | 3/2018 | Mustakos et al. |
| 2018/0104482 A1 | 4/2018 | Bokil |
| 2018/0110971 A1 | 4/2018 | Serrano Carmona |
| 2018/0154152 A1* | 6/2018 | Chabrol ............... A61N 5/0622 |
| 2018/0193655 A1 | 7/2018 | Zhang et al. |
| 2018/0229042 A1 | 8/2018 | Kaula et al. |
| 2018/0243570 A1 | 8/2018 | Malinowski et al. |

(56) References Cited

U.S. PATENT DOCUMENTS

| | | |
|---|---|---|
| 2018/0256906 A1 | 9/2018 | Pivonka et al. |
| 2018/0318578 A1 | 11/2018 | Ng et al. |
| 2018/0326219 A1 | 11/2018 | Wolf, II |
| 2018/0369606 A1 | 12/2018 | Zhang et al. |
| 2018/0369607 A1 | 12/2018 | Zhang et al. |
| 2018/0369608 A1 | 12/2018 | Chabrol |
| 2019/0003898 A1 | 1/2019 | Dehkhoda et al. |
| 2019/0201709 A1 | 7/2019 | Tischendorf et al. |
| 2019/0209834 A1 | 7/2019 | Zhang et al. |
| 2019/0209849 A1 | 7/2019 | Hershey et al. |
| 2019/0209850 A1 | 7/2019 | Steinke |
| 2020/0001096 A1 | 1/2020 | Zhang et al. |
| 2020/0094047 A1 | 3/2020 | Govea et al. |
| 2020/0155584 A1 | 5/2020 | DiMauro |
| 2020/0155854 A1 | 5/2020 | Leven et al. |
| 2020/0271796 A1 | 8/2020 | Tahon et al. |
| 2020/0323589 A1 | 10/2020 | Varol |
| 2020/0376262 A1 | 12/2020 | Clark et al. |
| 2020/0376272 A1 | 12/2020 | Block et al. |
| 2021/0008388 A1 | 1/2021 | Vansickle et al. |
| 2021/0008389 A1 | 1/2021 | Featherstone et al. |
| 2021/0016111 A1 | 1/2021 | Vansickle et al. |
| 2022/0054226 A1 | 2/2022 | Gregg, II et al. |
| 2022/0072329 A1 | 3/2022 | Howard |
| 2022/0323781 A1 | 10/2022 | Subramanian et al. |
| 2022/0339448 A1 | 10/2022 | Jayakumar et al. |
| 2024/0058619 A1 | 2/2024 | Zhu et al. |
| 2024/0220094 A1 | 7/2024 | Howard et al. |
| 2024/0226596 A1 | 7/2024 | Carbunaru et al. |

FOREIGN PATENT DOCUMENTS

| | | |
|---|---|---|
| WO | 02/091935 | 11/2002 |
| WO | 2008118042 | 10/2008 |
| WO | 2010029297 | 3/2010 |
| WO | 2011/031131 | 3/2011 |
| WO | 2011/150430 | 12/2011 |
| WO | 2012/103543 | 8/2012 |
| WO | 2014081449 | 5/2014 |
| WO | 2014143387 | 9/2014 |
| WO | 2015164571 | 10/2015 |
| WO | 2019/183054 | 9/2019 |
| WO | 2019/183068 | 9/2019 |
| WO | 2019/183075 | 9/2019 |
| WO | 2019/183078 | 9/2019 |
| WO | 2021141163 | 7/2021 |

OTHER PUBLICATIONS

Chow, Roberta et al., Roberta et al., Inhibitory Effects of Laser Irradiation on Peripheral Mammalian Nerves and Relevance to Analgesic Effects: A Systematic Review, Photomedicine and Laser Surgery (2011) 29:6, 365-381.

Kono, Toru et al., Cord Dorsum Potentials Suppressed by Low Power Laser Irradiation on a Peripheral Nerve in the Cat, Journal of Clinical Laser Medicine & Surgery (1993) 11:3, 115-118.

Snyder-Mackler, Lynn et al., Effect of Helium-Neon Laser Irradiation on Peripheral Sensory Nerve Latency, Phys. Ther. (1988), 68:223-225.

U.S. Appl. No. 12/177,823, Entitled: Lead With Transition and Methods of Manufacture and Use, Inventor: Pianca et al., filed Jul. 22, 2008, 22 pages.

U.S. Appl. No. 13/750,725, Entitled: Systems and Methods for Identifying the Circumferential Positioning of Electrodes of Leads for Electrical Stimulation Systems, Inventor: Pianca et al., filed Jan. 25, 2013, 36 pages.

U.S. Appl. No. 62/292,083, Entitled: Implantable Optical Stimulation Lead and Methods of Making and Using, Inventor: Orinski, filed Feb. 5, 2016, 29 pages.

U.S. Appl. No. 62/424,130, Entitled: Implantable Optical Stimulation Lead and Methods of Making and Using, Inventor: Orinski, filed Nov. 18, 2016, 34 pages.

U.S. Appl. No. 13/902,749, Entitled: Low-Level Laser Therapy, Inventor: Zhu et al., filed May 24, 2013, 66 pages.

U.S. Appl. No. 13/902,754, Entitled: Combination Electrical Stimulation and Low-Level Laser Therapy, Inventor: Zhu et al., filed May 24, 2013, 70 pages.

U.S. Appl. No. 15/450,969, Entitled: Implantable Optical Stimulation Leads and Methods of Making and Using, Inventor: Joshua Dale Howard, filed Mar. 6, 2017, 29 pages.

U.S. Appl. No. 62/411,203, Entitled: Electrical Stimulation Methods With Optical Observation and Devices Therefor, Inventor: Raul Enrique Serrano Carmona, filed Oct. 21, 2016, 41 pages.

Darlot, Fannie et al., Near-infrared light is neuroprotective in a monkey model of Parkinson's disease (2006), 30 pages.

International Search Report and Written Opinion from International Patent Application No. PCT/US2017/015846, mailed May 3, 2017.

Micah S Siegel, Ehud Y Isacoff, A Genetically Encoded Optical Probe of Membrane Voltage, Neuron, vol. 19, Issue 4, Oct. 1997, pp. 735-741, ISSN 0896-6273, http://dx.doi.org/10.1016/S0896-6273(00)80955-1.

Barnett L, Platisa J, Popovic M, Pieribone VA, Hughes T. A Fluorescent, Genetically-Encoded Voltage Probe Capable of Resolving Action Potentials. (2012) (http://www.sciencedirect.com/science/article/pii/S0896627300809551).

Brennan KC, Toga AW. Intraoperative Optical Imaging. In: Frostig RD, editor. In Vivo Optical Imaging of Brain Function. 2nd edition. Boca Raton (FL): CRC Press/Taylor & Francis; 2009. Chapter 13. Available from: http://www.ncbi.nlm.nih.gov/books/NBK20224/.

Use of NAD(P)H and flavoprotein autofluorescence transients to probe neuron and astrocyte responses to synaptic activation. Shuttleworth 2010 Neurochemestry international.

Official Communication for U.S. Appl. No. 15/421,001 mailed Oct. 18, 2018.

Official Communication for U.S. Appl. No. 15/421,001 mailed Jan. 10, 2019.

Official Communication for U.S. Appl. No. 16/412,157 mailed Dec. 9, 2021.

Official Communication for U.S. Appl. No. 16/412,157 mailed Jun. 16, 2022.

Vallejo, Ricardo, Kerry Bradley, and Leonardo Kapural. "Spinal cord stimulation in chronic pain: Mode of action." Spine 42 (2017): S53-S60.

Vivianne L. Tawfik, Su-Youne Chang, Frederick L. Hitti, David W. Roberts, James C. Leiter, Svetlana Jovanovic, Kendall H. Lee, Deep Brain Stimulation Results in Local Glutamate and Adenosine Release: Investigation Into the Role of Astrocytes, Neurosurgery, vol. 67, Issue 2, Aug. 2010, pp. 367-375, https://doi.org/10.1227/01.NEU.0000371988.73620.4C.

U.S. Appl. No. 18/232,649, filed Aug. 10, 2023.

U.S. Appl. No. 18/232,621, filed Aug. 10, 2023.

Weiran Cao, Jian Li, Hongzheng Chen, Jiangeng Xue, "Transparent electrodes for organic optoelectronic devices: a review," J. Photon. Energy 4(1) 040990 (Oct. 30, 2014) https://doi.org/10.1117/1.JPE.4.040990.

Lee KT, Park DH, Baac HW, Han S. Graphene- and Carbon-Nanotube-Based Transparent Electrodes for Semitransparent Solar Cells. Materials (Basel). Aug. 22, 2018;11(9):1503. doi: 10.3390/ma11091503. PMID: 30135379; PMCID: PMC6165141.

R G Wilson, "Ball-lens coupling efficiency for laser-diode to single-mode fiber: comparison of independent studies by distinct methods," Applied Optics May 20, 1998, 37 (15): 3201-5.

\* cited by examiner

IMPLANTABLE OPTICAL STIMULATION LEAD AND METHODS OF MAKING AND USING

CROSS-REFERENCE TO RELATED APPLICATIONS

This application is a continuation of U.S. patent application Ser. No. 16/412,157, filed May 14, 2019, which is a continuation of U.S. patent application Ser. No. 15/421,001, filed Jan. 31, 2017, which issued as U.S. Pat. No. 10,335,607 on Jul. 2, 2019, which claims priority to U.S. Provisional Patent Application Ser. No. 62/292,083, filed Feb. 5, 2016, and U.S. Provisional Patent Application Ser. No. 62/424,130, filed Nov. 18, 2016, all of which are incorporated herein by reference in their entirety.

FIELD

The present invention is directed to the area of implantable optical stimulation systems and methods of making and using the systems. The present invention is also directed to implantable optical stimulation leads having a light source at the distal end of the lead, as well as methods of making and using the leads and optical stimulation systems.

BACKGROUND

Implantable optical stimulation systems can provide therapeutic benefits in a variety of diseases and disorders. For example, optical stimulation can be applied to the brain either externally or using an implanted stimulation lead to provide, for example, deep brain stimulation, to treat a variety of diseases or disorders. Optical stimulation may also be combined with electrical stimulation.

Stimulators have been developed to provide therapy for a variety of treatments. A stimulator can include a control module (for generating light or electrical signals sent to light sources in a lead), one or more leads, and one or more light sources coupled to, or disposed within, each lead. The lead is positioned near the nerves, muscles, or other tissue to be stimulated.

BRIEF SUMMARY

One embodiment is an optical stimulation lead including a lead body including a distal end, a distal portion, and a proximal portion; and an optical assembly attached to the distal end of the lead body. The optical assembly includes a light emitter; a feedthrough assembly including at least one ceramic block, at least one feedthrough pin extending through the at least one ceramic block and electrically coupled to the light emitter, and a metal housing attached to the at least one ceramic block; a metal tube attached to the feedthrough assembly and disposed around the light emitter; and an emitter cover disposed over the light emitter and coupled to the metal tube.

In at least some embodiments, the optical assembly forms a hermetically sealed housing for the light emitter. In at least some embodiments, the optical assembly further includes an anchor extending proximally from the feedthrough assembly, where the anchor is configured and arranged to be inserted into the distal end of the lead body to anchor the optical assembly to the lead body. In at least some embodiments, the anchor includes a proximally tapered flange to facilitate attachment of the anchor to the lead body. In at least some embodiments, the lead body defines a lumen to receive at least a portion of the anchor to facilitate attachment of the anchor to the lead body. In at least some embodiments, the at least one ceramic block is attached to the anchor with a braze joint.

In at least some embodiments, the at least one ceramic block is attached to the metal housing with a braze joint. In at least some embodiments, the at least one ceramic block is attached to the at least one feedthrough pin with a braze joint. In at least some embodiments, the optical stimulation lead further includes at least one lead cable disposed within the optical assembly to electrically couple the at least one feedthrough pin to the light emitter.

In at least some embodiments, the at least one ceramic block is attached to the anchor to form a hermetic seal. In at least some embodiments, the at least one ceramic block is attached to the metal housing to form a hermetic seal. In at least some embodiments, the at least one ceramic block is attached to the at least one feedthrough pin to form a hermetic seal.

In at least some embodiments, the optical stimulation lead further includes terminals disposed along the proximal portion of the lead body and conductors extending along the lead body, where at least one of the conductors electrically couples the at least one feedthrough pin to at least one of the terminals of the lead. In at least some embodiments, the optical stimulation lead further includes at least one electrode disposed along the distal portion of the lead body. In at least some embodiments, at least one of the conductors electrically couples the at least one electrode to at least one of the terminals of the lead. In at least some embodiments, the lead body defines a lumens extending along the lead body, where the conductors are disposed in at least one of the lumens.

In at least some embodiments, the emitter covering is an optical diffuser. In at least some embodiments, the emitter covering is a lens.

Another embodiment is an optical stimulation system including any of the optical stimulation leads described above and a control module coupleable to the optical stimulation lead. The control module includes a housing and an electronic subassembly disposed in the housing to provide electrical signals to the light emitter of the optical stimulation lead.

In at least some embodiments, the lead further includes terminals disposed along the proximal portion of the lead body and the optical stimulation system further includes a connector for receiving the proximal portion of the lead body, the connector having a proximal end, a distal end, and a longitudinal length, the connector including a connector housing defining a port at the distal end of the connector, the port configured and arranged for receiving the proximal portion of the lead body of the optical stimulation lead, and connector contacts disposed in the connector housing, the connector contacts configured and arranged to couple to the terminals disposed along the proximal portion of the lead body of the optical stimulation lead.

In at least some embodiments, the connector is part of the control module. In at least some embodiments, the electrical stimulation system further includes a lead extension coupleable to both the electrical stimulation lead and the control module, where the connector is part of the lead extension.

Yet another embodiment is a method of stimulating patient tissue that includes implanting any of the optical stimulation leads described above into the patient tissue; and emitting light from the light emitter of the optical stimulation lead to stimulate the patient tissue.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable optical stimulation systems and methods of making and using the systems. The present invention is also directed to implantable optical stimulation leads having a light source at the distal end of the lead, as well as methods of making and using the leads and optical stimulation systems.

In some embodiments, the implantable optical stimulation system only provides optical stimulation. In other embodiments, the stimulation system can include both optical and electrical stimulation. In at least some of these embodiments, the optical stimulation system can be a modification of an electrical stimulation system to also provide optical stimulation. Suitable implantable electrical stimulation systems that can be modified to also provide optical stimulation include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference in their entireties.

Figure 1:
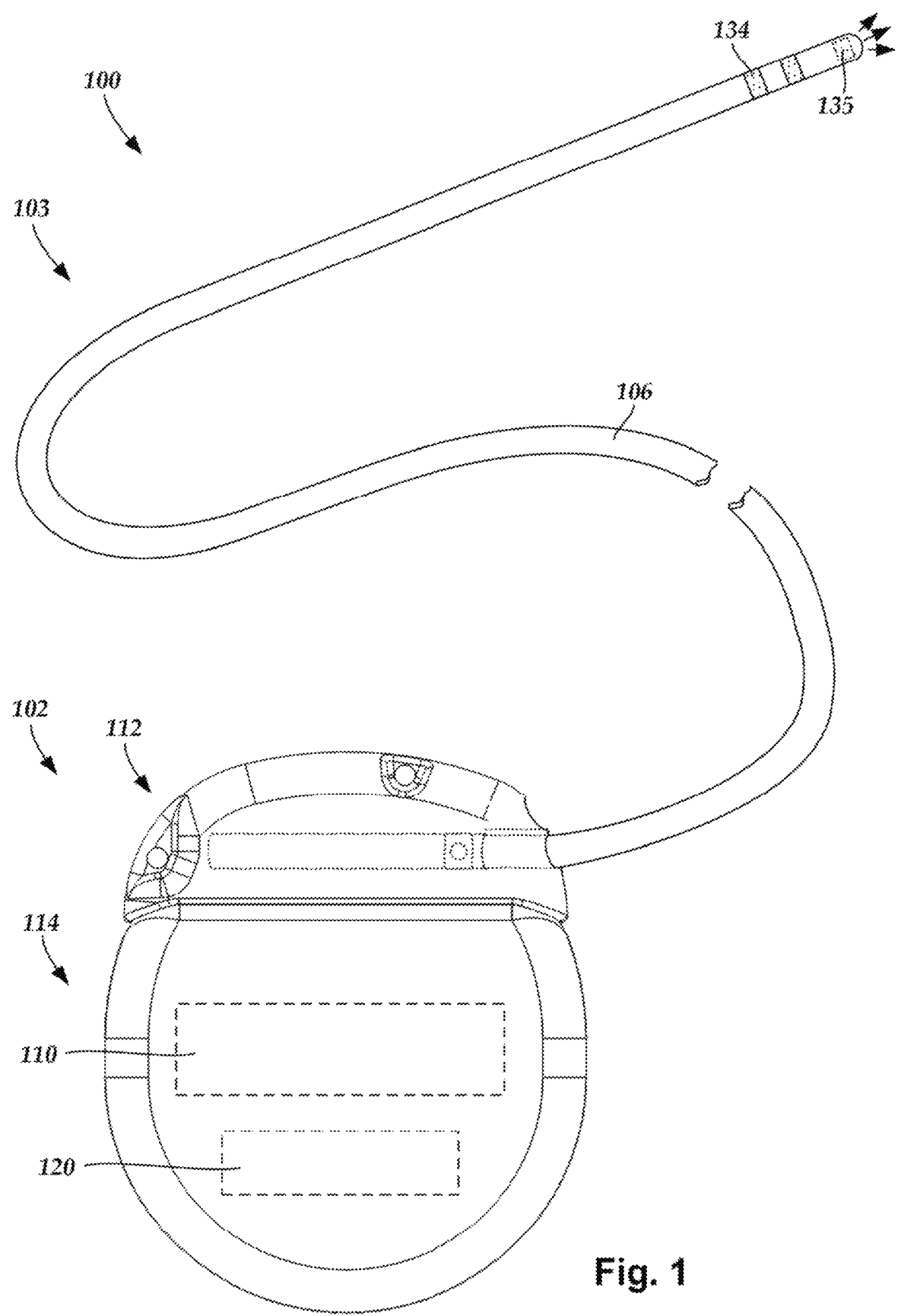
FIG. 1 is a schematic side view of one embodiment of an optical stimulation system that includes a lead electrically coupled to a control module, according to the invention.
Figure 2A:
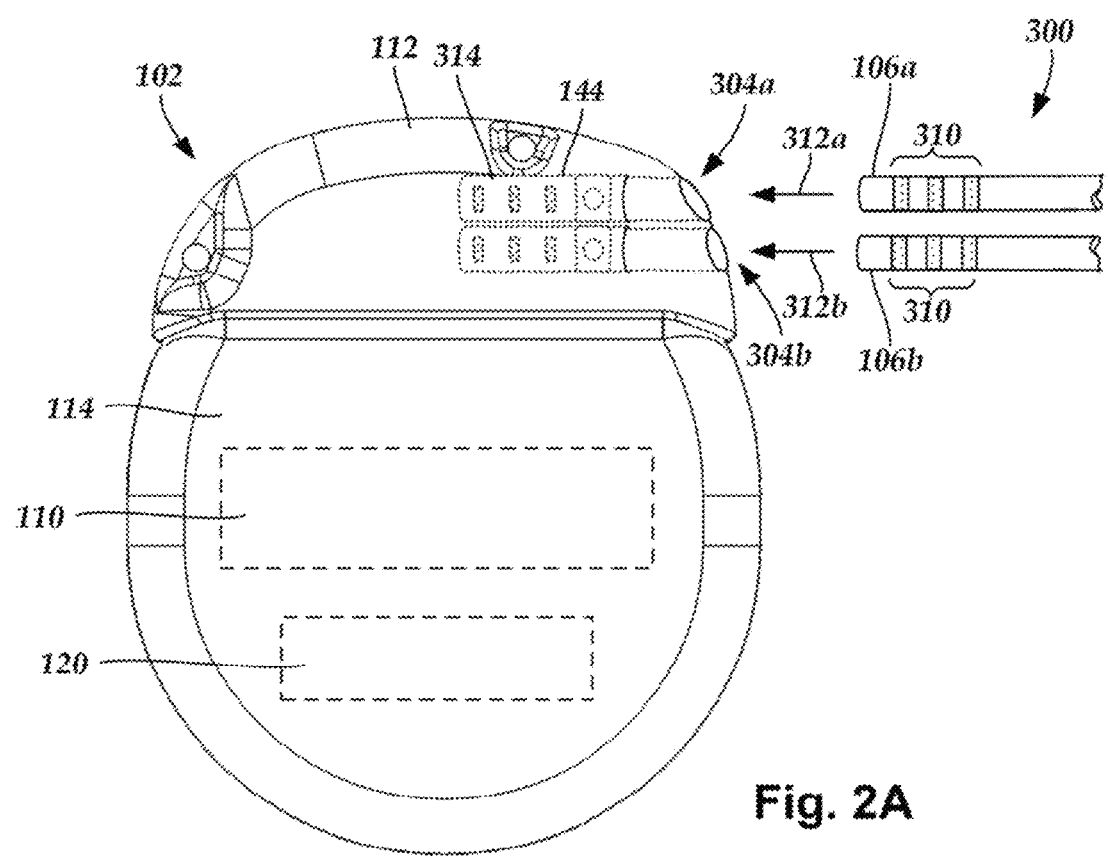
FIG. 2A is a schematic side view of one embodiment of the control module of FIG. 1 configured and arranged to couple to an elongated device, according to the invention.
Figure 2B:
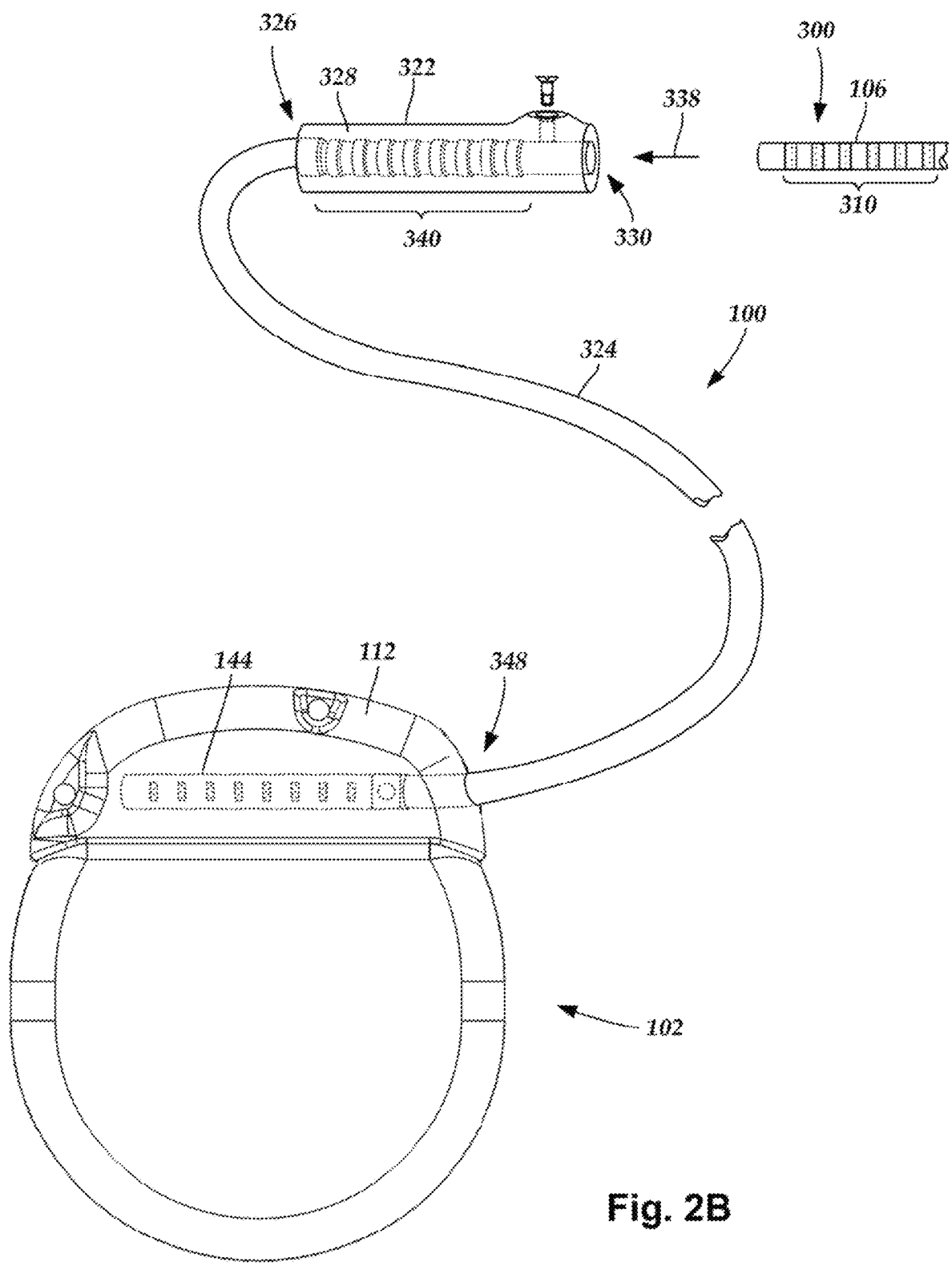
FIG. 2B is a schematic side view of one embodiment of a lead extension configured and arranged to couple the elongated device of FIG. 2A to the control module of FIG. 1, according to the invention.

FIG. 1 illustrates schematically one embodiment of an optical stimulation system 100. The optical stimulation system includes a control module (e.g., a stimulator) 102 and a lead 103 coupleable to the control module 102. The lead 103 includes one or more lead bodies 106. In FIG. 1, the lead 103 is shown having a single lead body 106. In FIG. 2B, the lead 103 includes two lead bodies. It will be understood that the lead 103 can include any suitable number of lead bodies including, for example, one, two, three, four, five, six, seven, eight or more lead bodies 106.

At least one light emitter 135 is provided at a distal end of the lead 103. The light emitter 135 can be a light source, such as a light emitting diode (LED), laser diode, organic light emitting diode (OLED), or the like. Optionally, the lead can also include one or more electrodes 134 disposed along the lead body 106, and one or more terminals (e.g., 310 in FIG. 2A-2B) disposed along each of the one or more lead bodies 106 and coupled to the optional electrodes 134 by conductors (not shown). In at least some embodiments, one or more terminals (e.g., 310 in FIG. 2A-2B) may also be used to convey electrical signals to a light source that acts as the light emitter 135 by conductors (not shown) extending along the lead.

The lead 103 can be coupled to the control module 102 in any suitable manner. In some embodiments, the lead is permanently attached to the control module 102. In other embodiments, the lead can be coupled to the control module 102 by a connector (e.g., connector 144 of FIG. 2A). In FIG. 2A, the lead 103 is shown coupling directly to the control module 102 through the connector 144. In at least some other embodiments, the lead 103 couples to the control module 102 via one or more intermediate devices, as illustrated in FIG. 2B. For example, in at least some embodiments one or more lead extensions 324 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the stimulation system 100 includes multiple elongated devices disposed between the lead 103 and the control module 102, the intermediate devices may be configured into any suitable arrangement.

The control module 102 can include, for example, a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The stimulation system or components of the stimulation system, including the lead 103 and the control module 102, are typically implanted into the body of a patient. The stimulation system can be used for a variety of applications including, but not limited to brain stimulation, deep brain stimulation, neural stimulation, spinal cord stimulation, muscle stimulation, and the like.

If the lead includes the optional electrodes 134, the electrodes can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. Any suitable number of electrodes 134 can be disposed on the lead including, for example, one, two, three, four, five, six, seven, eight, nine, ten, eleven, twelve, fourteen, sixteen, twenty-four, thirty-two, or more electrodes 134.

The one or more lead bodies 106 are made of a non-conductive, biocompatible material such as, for example, silicone, polyurethane, polyetheretherketone ("PEEK"), epoxy, and the like or combinations thereof. The one or more lead bodies 106 may be formed in the desired shape by any process including, for example, molding (including injection molding), casting, and the like.

One or more terminals (e.g., 310 in FIGS. 2A-2B) are typically disposed along the proximal end of the one or more lead bodies 106 of the stimulation system 100 (as well as any splitters, lead extensions, adaptors, or the like) for electrical connection to corresponding connector contacts (e.g., 314 in FIGS. 2A-2B). The connector contacts are disposed in connectors (e.g., 144 in FIGS. 1-2B; and 322 FIG. 2B) which, in turn, are disposed on, for example, the control module 102 (or a lead extension, a splitter, an adaptor, or the like). Electrically conductive wires, cables, or the like (not shown) extend from the terminals to the light emitter 135 or optional one or more electrodes 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 2B, an adaptor, or the like or combinations thereof), or a combination thereof.

The control module connector 144 defines at least one port into which a proximal end of the elongated device 300 can be inserted, as shown by directional arrows 312a and 312b. In FIG. 2A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Each of the terminals 310 can couple to the light emitter 135 or one or more of the optional electrodes 134. Examples of connectors in control modules are found in, for example, U.S. Pat. Nos. 7,244,150 and 8,224,450, which are incorporated by reference.

FIG. 2B is a schematic side view of another embodiment of the stimulation system 100. The stimulation system 100 includes a lead extension 324 that is configured and arranged to couple one or more elongated devices 300 (e.g., one of the lead bodies 106 of FIG. 1, a splitter, an adaptor, another lead extension, or the like or combinations thereof) to the control module 102. In FIG. 2B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144 (e.g., the ports 304a and 304b of FIG. 1), or to receive multiple elongated devices 300 (e.g., both of the lead bodies 106 of FIG. 1), or both.

A lead extension connector 322 is disposed on the lead extension 324. In FIG. 2B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. Each of the terminals 310 can couple to the light emitter 135 or one or more of the optional electrodes 134. The connector housing 328 also includes a plurality of connector contacts, such as connector contact 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIG. 1) disposed along the lead (103 in FIG. 1).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 2B), the proximal end 348 of the lead extension 324 is configured and arranged for insertion into the control module connector 144.

Figure 3A:
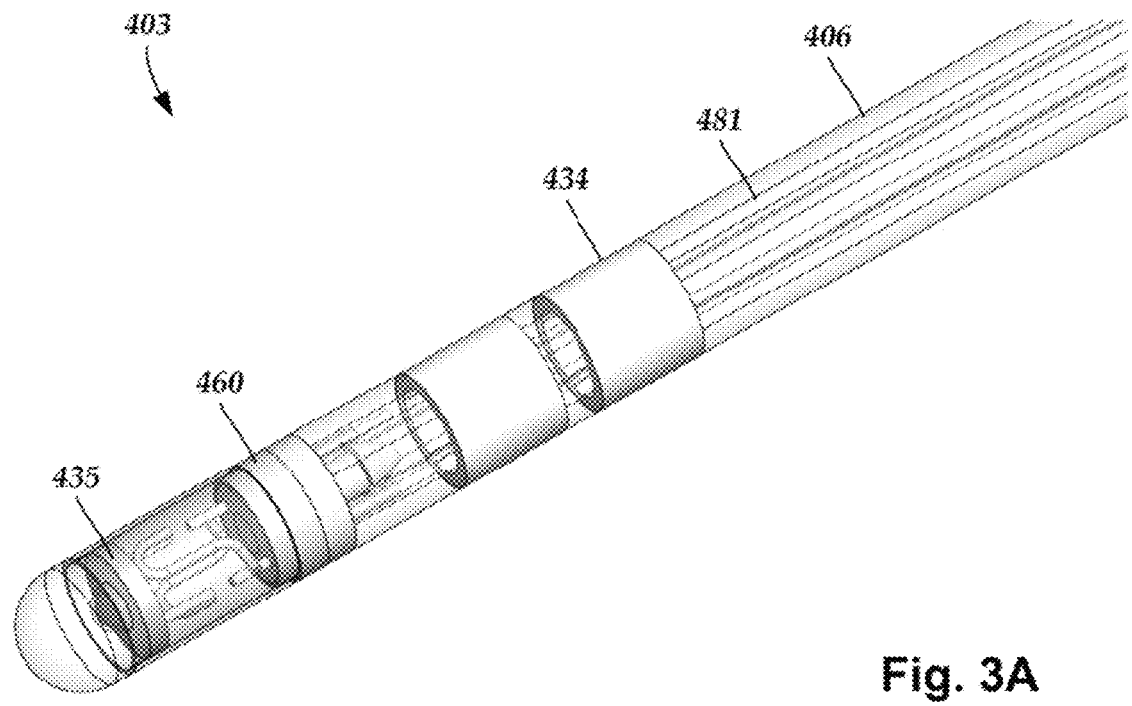
FIG. 3A is a schematic perspective view of one embodiment of a distal end of an optical stimulation lead with one embodiment of an optical assembly, according to the invention.
Figure 3B:
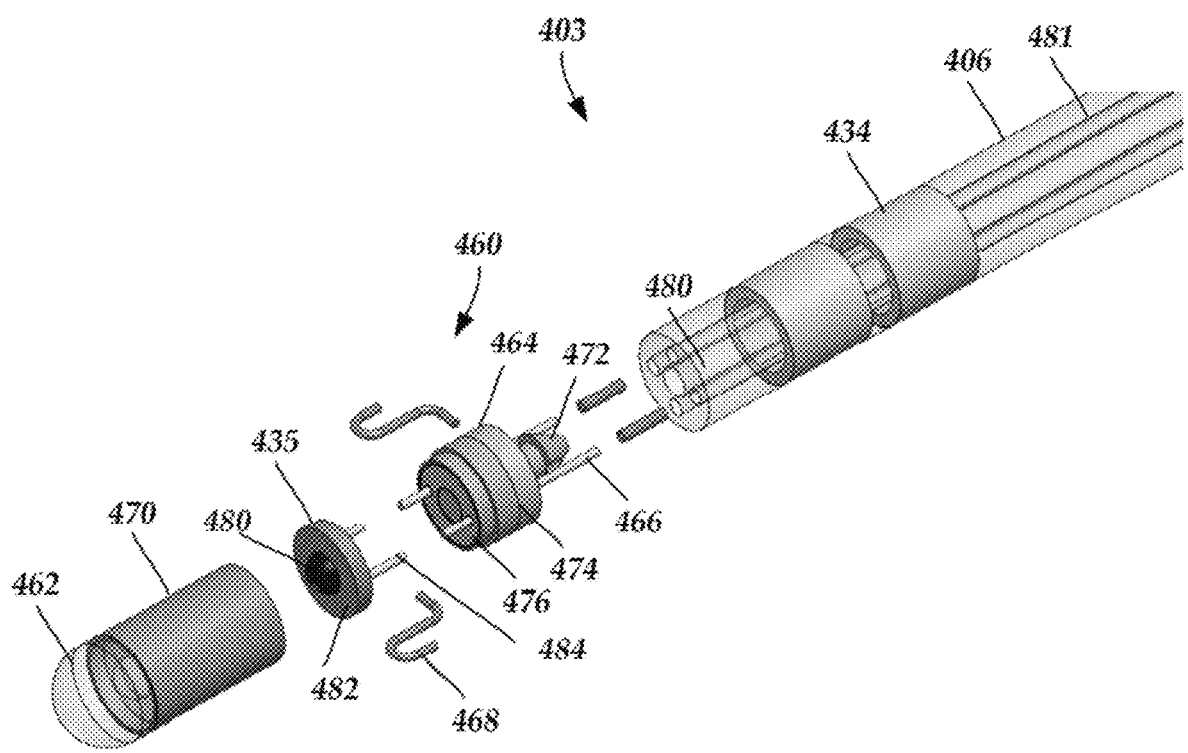
FIG. 3B is a schematic partially exploded view of the distal end of the optical stimulation lead of FIG. 3A, according to the invention.

FIG. 3A illustrates the distal end of one embodiment of a lead 403 with a lead body 406, an optical assembly 460 containing a light emitter 435 attached to the distal end of the lead body, and two optional electrodes 434 disposed along the lead body. FIG. 3B is an exploded view of the components of the optical assembly 460. In at least some embodiments, the optical assembly 460 provides a hermetically sealed housing for the light emitter 435.

In the illustrated embodiment of FIGS. 3A and 3B, the optical assembly 460 includes the light emitter 435, an emitter cover 462, a feedthrough assembly 464, feedthrough pins 466, conductive cables 468, a metal tube 470, and an anchor 472. The light emitter 435 emits light in response to electrical signals transmitted along the lead 403. Any suitable light emitter can be used including, but not limited to, a light emitting diode (LED), laser diode, organic light emitting diode (OLED), or the like. The light emitter 435 can emit one or more wavelengths of light or can emit light in one or more wavelength bands. The wavelength or wavelength band can be visible, infrared, or ultraviolet light. In at least some embodiments, the light emitter 435 emits visible light. In at least some embodiments, the light emitter 435 emits light at one or more wavelengths in a range of 500 to 800 nm or in a range of 600 to 700 nm. Although FIGS. 3A and 3B illustrate a single light emitter 435, it will be understood that other embodiments can include multiple light emitters. Those light emitters may emit light at a same wavelength or wavelength band or some, or all, of the light emitters may emit light at different wavelengths or wavelength bands.

In at least some embodiments, the light emitter 435 includes an emitter element 480, a flange 482 or other housing, and at least two contacts 484. The emitter element 480 may also include a protective material (such as a ceramic or polymeric material) disposed around the actual light emitting structure. The flange 482 can be made of any suitable material and may provide structural or positional stability for the emitter element 480 within the optical assembly 460. The contacts 484 can be pins, pads, or any other structure that provides for electrical coupling of the emitter element 480 to other components, such as the conductive cables 468 or feedthrough pins 466. The conductive cables 468 of the optical assembly 460 can be conductive wires, pins, or any other suitable conductive structure to electrically couple the contacts 484 of the light emitter 435 to the feedthrough pins 466. It will be understood that in other embodiments, the contacts 484 can be coupled directly to the feedthrough pins 466 without the use of conductive cables.

In at least some embodiments, an emitter cover 462 is disposed over the light emitter 435. In at least some embodiments, the emitter cover 462 can be an optical component such as an optical diffuser or lens. For example, a sapphire optical diffuser dome can be positioned over the light emitter. In other embodiments, the emitter cover 462 may be an optically transparent or translucent material to seal the light emitter 435 within the optical assembly 460. In some embodiments, the emitter cover 462 can be part of a package that forms the light emitter 435.

Figure 3C:
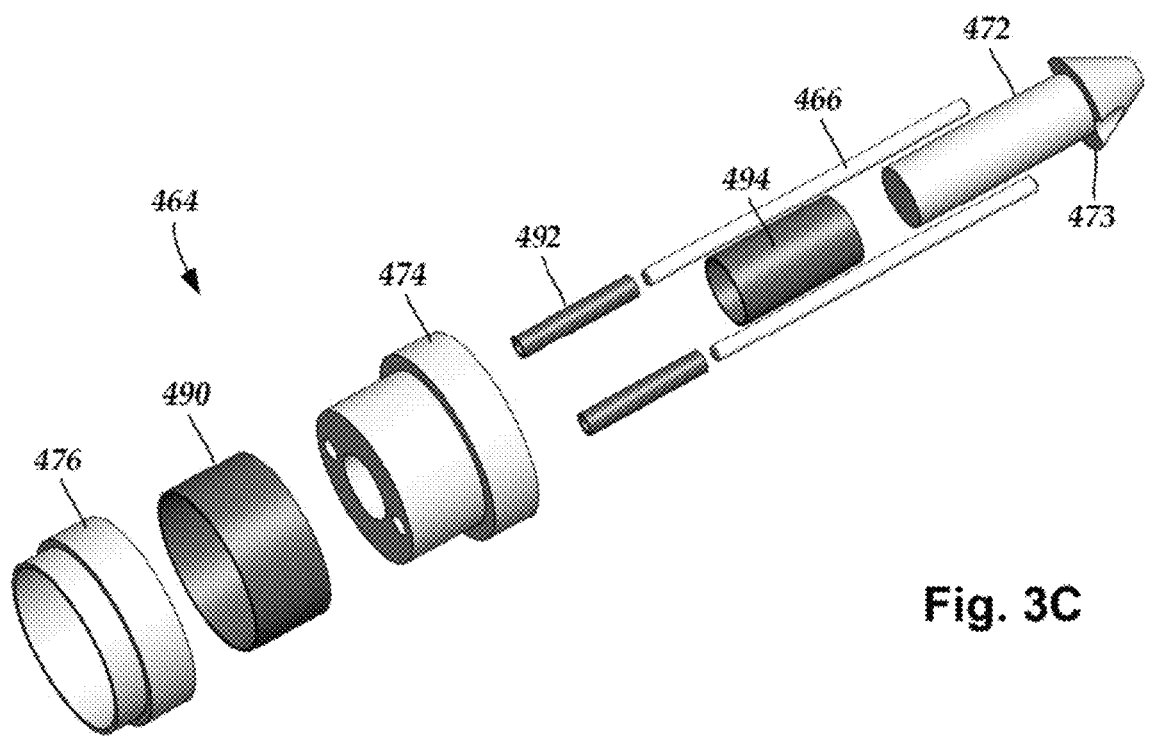
FIG. 3C is a schematic exploded view of the feedthrough assembly of the optical stimulation lead of FIG. 3A, according to the invention.

FIG. 3C illustrates an exploded view of one embodiment of the feedthrough assembly 464 which includes a ceramic block 474 through which the feedthrough pins 466 pass and a metal housing 476 surrounding a portion of the ceramic block. In at least some embodiments, the ceramic block 474 and metal housing 476 are physically attached together by a braze joint 490. For example, the metal housing 476 can be made of titanium and the braze joint 490 can be a gold (or gold alloy) braze joint. In other embodiments, other methods of attachment can be use such as, for example, an adhesive, or the ceramic block 474 and metal housing 476 may be coupled together by a frictional, interference, or compression fit or any combination thereof.

The feedthrough pins 466 are also made of metal. In at least some embodiments, the ceramic block 474 and feedthrough pins 466 are physically attached together by a braze joint 492. For example, the feedthrough pins 466 can be made of platinum, iridium, platinum/iridium alloy, or any other suitable material and the braze joint 490 can be a gold (or gold alloy) braze joint. In other embodiments, other methods of attachment can be use such as, for example, an adhesive, or the ceramic block 474 and feedthrough pins 466 may be coupled together by a frictional, interference, or compression fit or any combination thereof.

The anchor 472 is coupled to, and extends away from, the feedthrough assembly 464. The anchor 472 can be made of metal or any other suitable material and is shaped to fit into a lumen 480 in the lead body 406. The anchor 472 can be physical attached to the ceramic block 474 (or, in other embodiments, the metal housing 476) by a braze joint 494 (for example, a gold or gold alloy braze for a titanium anchor) or using adhesive or any other suitable attachment method or the ceramic block 474 and anchor 472 can be coupled by a frictional, interference, or compression fit, or any combination thereof. In at least some embodiments, the anchor 472 forms a frictional or compression fit with the lumen 480 of the lead body. In at least some embodiments, the polymeric material of the lead body 406 may be heated to allow the material to reflow around the anchor 472 to enhance the attachment of the anchor to the lead body. In at least some embodiments, the anchor 472 can include a flange 473 at the proximal end of the anchor to engage the lead body 406. In the illustrated body, the flange 473 tapers in a proximal direction to facilitate inserting the anchor 472 into the lumen 480 of the lead body 406.

Turning back to FIGS. 3A and 3B, a metal tube 470 is disposed around the light emitter 435 and coupled to the metal housing 476 of the feedthrough assembly 464. The metal housing 476 can be attached to the metal tube 470 by welding or any other suitable attachment method including, but not limited to, adhesive or a frictional, interference, or compression fit, or any combination thereof. The metal tube 470 can be attached to the optical diffuser or lens 462 by brazing, adhesive, or a frictional, interference, or compression fit, or any combination thereof.

In at least some embodiments, the optical assembly 460 provides a hermetically sealed housing for the light emitter 435 which prevents or resists the flow of fluids into the optical assembly 460. For example, the use of welding and brazing to couple the components of the optical assembly 460, as described above, may facilitate or provide the hermetical sealing of the optical assembly 460.

The lead body 406 of the illustrated embodiment includes a central lumen 480 and multiple peripheral lumens 481. As indicated above, the anchor 472 can be inserted into the distal portion of the central lumen 480. The central lumen may also be used for insertion of a stylet during implantation, as discussed above.

One or more of the peripheral lumens 481 can carry conductors (not shown), such as conductive wires or cables. In at least some embodiments, the feedthrough pins 466 can be inserted into one or more of the peripheral lumens 481 and can be coupled to the conductors carried in those lumens in order to transmit electrical signals from the control module through the conductors to the optical assembly 460. In at least some embodiments, conductors in one or more of the peripheral lumens 481 can also be coupled to the optional electrodes 434, as described above and in the references cited above.

Figure 4A:
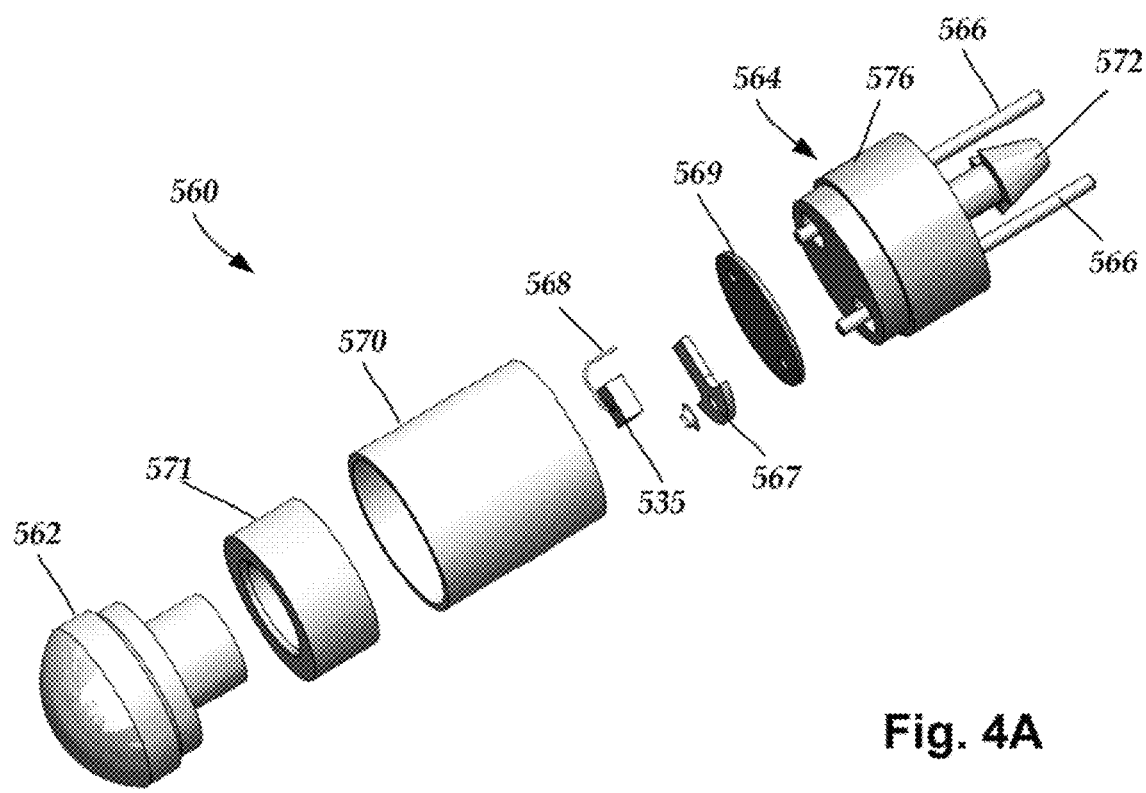
FIG. 4A is a schematic exploded view of another embodiment of an optical assembly for an optical stimulation lead, according to the invention.
Figure 4B:
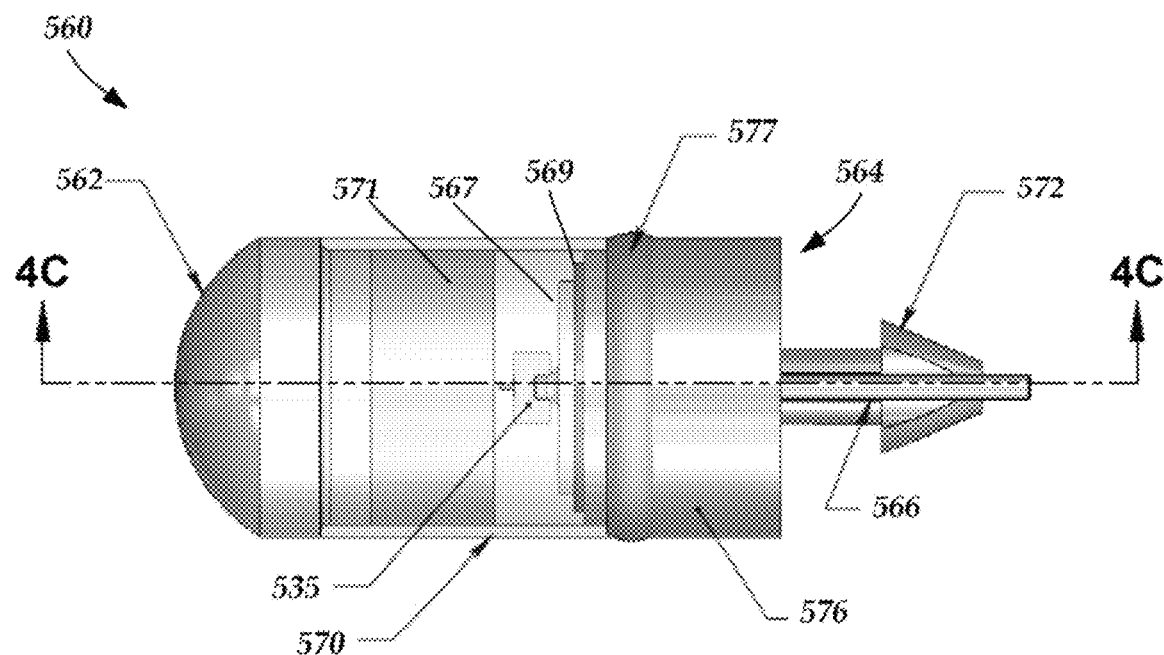
FIG. 4B is a schematic assembled side view of the optical assembly of FIG. 4A, according to the invention.
Figure 4C:
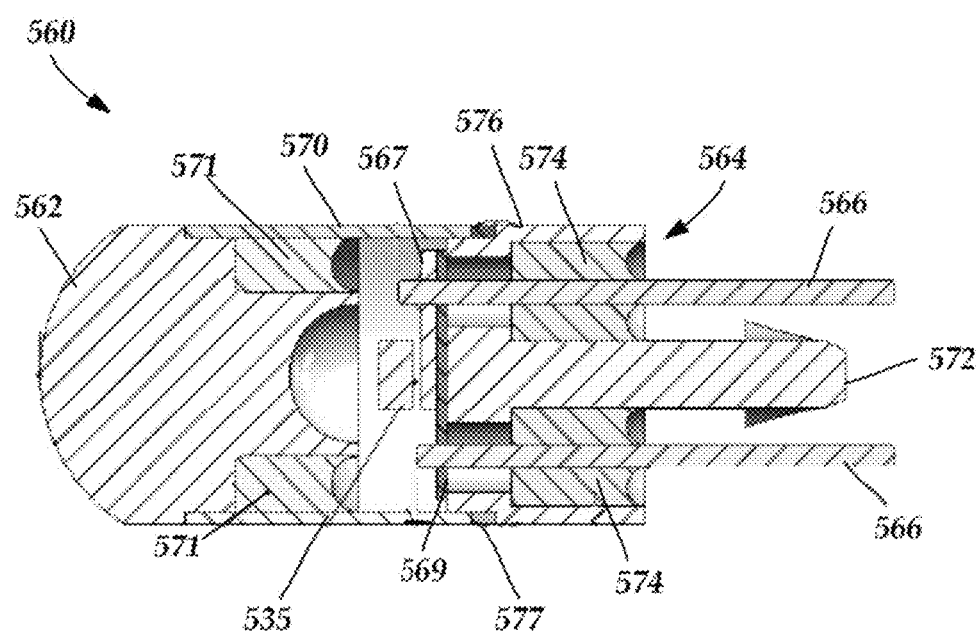
FIG. 4C is a schematic cross-sectional view of the optical assembly of FIG. 4A, according to the invention.

FIGS. 4A-4C illustrate another embodiment of an optical assembly 560 for a lead 403 (FIG. 3A). The optical assembly includes a light emitter 535, an emitter cover 562, a feedthrough assembly 564, one or more feedthrough pins 566, a connector plate 567, an insulator disc 569, a metal tube 570, a distal seal 571, and an anchor 572. The light emitter 535 emits light in response to electrical signals transmitted along the lead 403. The anchor 572 is similar to anchor 472 described above and can be attached to the lead 403 using any of the same methods and arrangements described above.

FIG. 4A is an exploded view and FIG. 4B is an assembled view of the optical assembly 560. FIG. 4C is a cross-sectional view of the optical assembly 560 and further illustrates that the feedthrough assembly 564 includes two ceramic blocks 574 (although in other embodiments, a single ceramic block forming an annulus around the anchor 572 can be used) through which the feedthrough pins 566 pass and a metal housing 576 surrounding the ceramic blocks. A joint 577 (FIGS. 4B and 4C) (for example, a weld joint) is formed between the metal tube 570 and metal housing 576. In at least some embodiments, the ceramic blocks 574 and metal housing 576 are physically or chemically attached together to form a seal or, preferably, a hermetic seal. For example, the metal housing 576 can be made of titanium or other metal and the ceramic blocks 574 can be made of Kryoflex™ (available from PA&E, Wenatchee, WA) or other ceramic material that can form a hermetic seal with the metal housing when both are fired or otherwise chemically activated. In other embodiments, the metal housing 576 and ceramic blocks 574 can be joined to form a seal (or, in some embodiments, a hermetic seal) by brazing or other joining techniques such as, for example, an adhesive, or the ceramic blocks 574 and metal housing 576 may be coupled together by a frictional, interference, or compression fit or any combination thereof.

The feedthrough pins 466 and the anchor 462 are made of metal and can be joined to the ceramic blocks 574 using the same methods of joining as described above for joining the metal housing 576 and ceramic blocks 574. Similarly, the proximal seal 572 can be made of a ceramic material, such as Kryoflex™, and can be joined to the metal tube 570 (which is made of titanium or other metal) using the same methods of joining as described above for joining the metal housing 576 and ceramic blocks 574. The metal tube 570 and metal housing 576 are then joined by welding or other suitable joining techniques.

Any suitable light emitter 535 can be used including, but not limited to, the light emitters described above for use as light emitter 435. In at least some embodiments, the light emitter 535 includes an emitter element, a housing, and at least two contacts, as describe above for light emitter 535. The contacts of the light emitter can be pins, pads, or any other structure. One contact is coupled to one of the feedback pins 566 (directly or through a conductor 568 illustrated in FIG. 4A) and the other contact is coupled to the other feedback pin 566 using the conductor plate 567 (for example, a nickel conductor plate) and, optionally, a conductive adhesive, conductive wire, or the like. An insulator disc 569 (for example, a disc made of Kapton™) is provided under conductor plate 567 to provide insulation between the two feedback pins 566 and the metal housing 576 of the feedback assembly 564.

In at least some embodiments, an emitter cover 562 is disposed over the light emitter 535. In at least some embodiments, the emitter cover 562 can be an optical component such as an optical diffuser or lens. For example, a sapphire optical diffuser dome can be positioned over the light emitter. In other embodiments, the emitter cover 562 may be an optically transparent or translucent material to seal the light emitter 535 within the optical assembly 560. In some embodiments, the emitter cover 562 can be part of a package that forms the light emitter 535.

In at least some embodiments, the optical assembly 560 provides a hermetically sealed housing for the light emitter 535 which prevents or resists the flow of fluids into the optical assembly 560. For example, the use of welding, brazing, or Kryoflex™ or combinations thereof to couple the components of the optical assembly 560, as described above, may facilitate or provide the hermetical sealing of the optical assembly 560.

Figure 5:
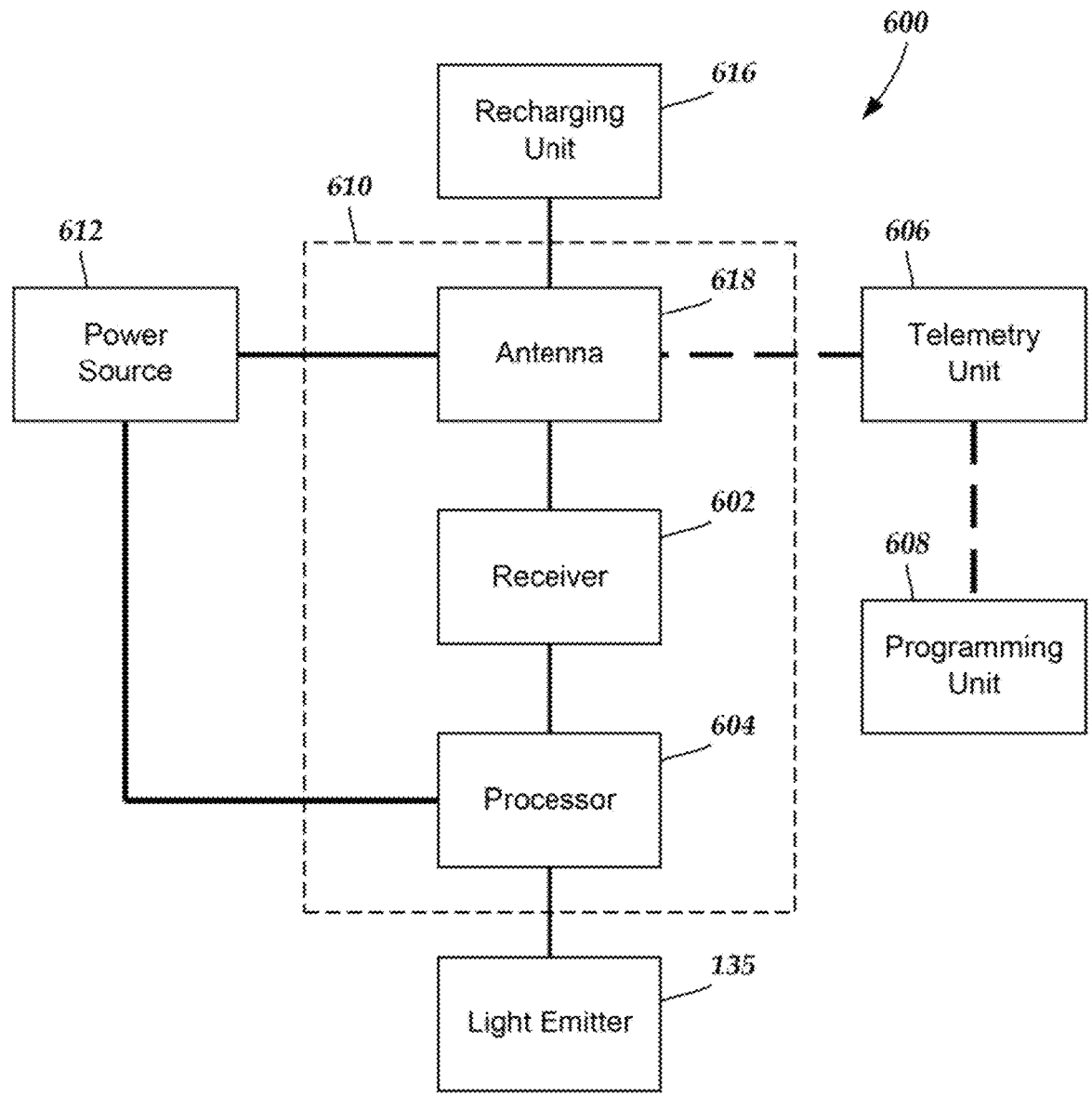
FIG. 5 is a schematic overview of one embodiment of components of an optical stimulation system, including an electronic subassembly disposed within a control module, according to the invention.

FIG. 5 is a schematic overview of one embodiment of components of an optical stimulation system 500 including an electronic subassembly 610 disposed within a control module. It will be understood that the optical stimulation system can include more, fewer, or different components and can have a variety of different configurations including those configurations disclosed in the stimulator references cited herein.

Some of the components (for example, a power source 612, an antenna 618, a receiver 602, and a processor 604) of the optical stimulation system can be positioned on one or more circuit boards or similar carriers within a sealed housing of an implantable pulse generator, if desired. Any power source 612 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 618 or a secondary antenna. The external power source can be in a device that is mounted on the skin of the user or in a unit that is provided near the user on a permanent or periodic basis.

If the power source 612 is a rechargeable battery, the battery may be recharged using the optional antenna 618, if desired. Power can be provided to the battery for recharging by inductively coupling the battery through the antenna to a recharging unit 616 external to the user. Examples of such arrangements can be found in the references identified above.

In one embodiment, light is emitted by the light emitter 135 of the lead body to stimulate nerve fibers, muscle fibers, or other body tissues near the optical stimulation system. The processor 604 is generally included to control the timing and other characteristics of the optical stimulation system.

For example, the processor 604 can, if desired, control one or more of the timing, pulse frequency, strength, duration, and waveform of the optical stimulation. In addition, the processor 604 can select one or more of the optional electrodes to provide electrical stimulation, if desired. In some embodiments, the processor 604 selects which of the optional electrode(s) are cathodes and which electrode(s) are anodes.

Any processor can be used and can be as simple as an electronic device that, for example, produces optical stimulation at a regular interval or the processor can be capable of receiving and interpreting instructions from an external programming unit 608 that, for example, allows modification of stimulation characteristics. In the illustrated embodiment, the processor 604 is coupled to a receiver 602 which, in turn, is coupled to the optional antenna 618. This allows the processor 604 to receive instructions from an external source to, for example, direct the stimulation characteristics and the selection of electrodes, if desired.

In one embodiment, the antenna 618 is capable of receiving signals (e.g., RF signals) from an external telemetry unit 606 which is programmed by the programming unit 608. The programming unit 608 can be external to, or part of, the telemetry unit 606. The telemetry unit 606 can be a device that is worn on the skin of the user or can be carried by the user and can have a form similar to a pager, cellular phone, or remote control, if desired. As another alternative, the telemetry unit 606 may not be worn or carried by the user but may only be available at a home station or at a clinician's office. The programming unit 608 can be any unit that can provide information to the telemetry unit 606 for transmission to the optical stimulation system 600. The programming unit 608 can be part of the telemetry unit 606 or can provide signals or information to the telemetry unit 606 via a wireless or wired connection. One example of a suitable programming unit is a computer operated by the user or clinician to send signals to the telemetry unit 606.

The signals sent to the processor 604 via the antenna 618 and the receiver 602 can be used to modify or otherwise direct the operation of the optical stimulation system. For example, the signals may be used to modify the stimulation characteristics of the optical stimulation system such as modifying one or more of stimulation duration, pulse frequency, waveform, and stimulation amplitude. The signals may also direct the optical stimulation system 600 to cease operation, to start operation, to start charging the battery, or to stop charging the battery. In other embodiments, the stimulation system does not include the antenna 618 or receiver 602 and the processor 604 operates as programmed.

Optionally, the optical stimulation system 600 may include a transmitter (not shown) coupled to the processor 604 and the antenna 618 for transmitting signals back to the telemetry unit 606 or another unit capable of receiving the signals. For example, the optical stimulation system 600 may transmit signals indicating whether the optical stimulation system 600 is operating properly or not or indicating when the battery needs to be charged or the level of charge remaining in the battery. The processor 604 may also be capable of transmitting information about the stimulation characteristics so that a user or clinician can determine or verify the characteristics.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. An optical stimulation lead, comprising:
   a lead body comprising a distal end, a distal portion, and a proximal portion; and
   an optical assembly attached to the distal end of the lead body and comprising
   a light emitter,
   a housing disposed around the light emitter and comprising an emitter cover disposed over the light emitter and a non-conductive feedthrough block disposed between the light emitter and the lead body; and
   a plurality of feedthrough pins extending through the non-conductive feedthrough block and electrically coupled to the light emitter.

2. The optical stimulation lead of claim 1, wherein the housing further comprises a metal ring coupled to the non-conductive feedthrough block.

3. The optical stimulation lead of claim 2, wherein the housing further comprises a metal tube coupled to the metal ring and the emitter cover.

4. The optical stimulation lead of claim 1, wherein the housing is hermetically sealed.

5. The optical stimulation lead of claim 1, wherein the light emitter comprises an emitter element and a flange disposed around the emitter element to provide structural or positional stability for the emitter element within the housing.

6. The optical stimulation lead of claim 1, wherein the optical assembly further comprises an anchor extending proximally from the housing, wherein the anchor is configured and arranged to be inserted into the distal end of the lead body to anchor the optical assembly to the lead body.

7. The optical stimulation lead of claim 6, wherein the anchor comprises a proximally tapered flange to facilitate attachment of the anchor to the lead body.

8. The optical stimulation lead of claim 7, wherein the lead body defines a lumen that is configured and arranged to receive at least a portion of the anchor to facilitate attachment of the anchor to the lead body.

9. The optical stimulation lead of claim 6, wherein the non-conductive feedthrough block is attached to the anchor.

10. The optical stimulation lead of claim 1, further comprising a plurality of conductive cables disposed within the optical assembly to electrically couple the feedthrough pins to the light emitter.

11. The optical stimulation lead of claim 1, further comprising a plurality of terminals disposed along the proximal portion of the lead body, wherein each of the feedthrough pins is electrically coupled to a different one of the terminals.

12. The optical stimulation lead of claim 1, wherein the non-conductive feedthrough block comprises a ceramic block.

13. The optical stimulation lead of claim 1, wherein the lead body defines a plurality of lumens extending along the lead body and conductors extending along at least one of the lumens, wherein each of the feedthrough pins is electrically coupled to at least one of the conductors.

14. The optical stimulation lead of claim 1, wherein the emitter cover comprises an optical diffuser.

15. The optical stimulation lead of claim 1, wherein the emitter cover comprises a lens.

16. An optical stimulation system, comprising:
the optical stimulation lead of claim 1; and
a control module coupleable to the optical stimulation lead, the control module comprising
a control module housing, and
an electronic subassembly disposed in the control module housing and configured and arranged to provide electrical signals to the light emitter of the optical stimulation lead.

17. The optical stimulation system of claim 16, wherein the optical stimulation lead further comprises a plurality of terminals disposed along the proximal portion of the lead body, the optical stimulation system further comprising a connector for receiving the proximal portion of the lead body, the connector having a proximal end, a distal end, and a longitudinal length, the connector comprising
a connector housing defining a port at the distal end of the connector, the port configured and arranged for receiving the proximal portion of the lead body of the optical stimulation lead, and
a plurality of connector contacts disposed in the connector housing, the plurality of connector contacts configured and arranged to couple to the plurality of terminals disposed along the proximal portion of the lead body of the optical stimulation lead.

18. The optical stimulation system of claim 17, wherein the connector is part of the control module.

19. The optical stimulation system of claim 17, further comprising a lead extension coupleable to both the optical stimulation lead and the control module, wherein the connector is part of the lead extension.

20. A method of stimulating patient tissue, the method comprising:
implanting the optical stimulation lead of claim 1 into the patient tissue; and
emitting light from the light emitter of the optical stimulation lead to stimulate the patient tissue.

\* \* \* \* \*